United States Patent
Kratzberg et al.

(10) Patent No.: US 9,198,787 B2
(45) Date of Patent: Dec. 1, 2015

(54) CONFORMABLE PROSTHESIS DELIVERY SYSTEM AND METHOD FOR DEPLOYMENT THEREOF

(75) Inventors: Jarin Kratzberg, Lafayette, IN (US); William Kurt Dierking, Louisville, KY (US); Sharath Gopalakrishnamurthy, Bangalore (IN); Blayne A. Roeder, Lafayette, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 561 days.

(21) Appl. No.: 13/331,935

(22) Filed: Dec. 20, 2011

(65) Prior Publication Data

US 2012/0172965 A1    Jul. 5, 2012

Related U.S. Application Data

(60) Provisional application No. 61/429,081, filed on Dec. 31, 2010.

(51) Int. Cl.
*A61F 2/06* (2013.01)
*A61F 2/962* (2013.01)
*A61F 2/966* (2013.01)
(Continued)

(52) U.S. Cl.
CPC . *A61F 2/962* (2013.01); *A61F 2/07* (2013.01); *A61F 2002/9511* (2013.01); *A61F 2002/9665* (2013.01)

(58) Field of Classification Search
CPC .............. A61F 2/07; A61F 2/95–2/97; A61F 2002/072–2002/077; A61F 2002/9505–2002/9665

USPC ....................... 623/1.11–1.13, 1.23
See application file for complete search history.

(56) References Cited

U.S. PATENT DOCUMENTS

| 6,346,118 | B1* | 2/2002 | Baker et al. ......... 623/1.12 |
| 6,613,072 | B2 | 9/2003 | Lau et al. |
| 7,335,224 | B2 | 2/2008 | Ohlenschlaeger |

(Continued)

FOREIGN PATENT DOCUMENTS

| EP | 2113225 | 11/2009 |
| WO | 00/78250 | 12/2000 |

OTHER PUBLICATIONS

Extended European Search Report, EP 11 27 5167, search completed Apr. 26, 2012.

(Continued)

*Primary Examiner* — Katherine Rodjom
*Assistant Examiner* — Jonathan Hollm
(74) *Attorney, Agent, or Firm* — Brinks Gilson & Lione

(57) ABSTRACT

A delivery system may include a stent-graft, a locking member, and one or more diameter reducing members. The stent-graft may include a tubular graft comprising first and second longitudinally extending sides disposed opposite each other and connected at a tangent line. When the locking member is in a locked position, the locking member restrains a surface of the graft against the cannula. The first diameter reducing member may be slidably connected to a first portion of the graft that is disposed proximate the tangent line and may be slidably connected to a second portion of the graft that is spaced circumferentially away from the tangent line. When the first diameter reducing member is in a restrained position, the second portion of the graft is drawn toward the first portion of the graft and the proximal portion of the stent-graft has a reduced diameter configuration with at least two lobes.

21 Claims, 11 Drawing Sheets

(51) Int. Cl.
  *A61F 2/07*    (2013.01)
  *A61F 2/95*    (2013.01)

(56) References Cited

U.S. PATENT DOCUMENTS

| | | | |
|---|---|---|---|
| 7,666,219 B2 | 2/2010 | Rasmussen et al. | |
| 7,722,657 B2 | 5/2010 | Hartley | |
| 7,758,626 B2 | 7/2010 | Kim et al. | |
| 8,206,427 B1 * | 6/2012 | Ryan et al. | 623/1.11 |
| 2003/0055484 A1 | 3/2003 | Lau et al. | |
| 2004/0073289 A1 * | 4/2004 | Hartley | 623/1.13 |
| 2004/0243215 A1 * | 12/2004 | Nelson | 623/1.12 |
| 2006/0004433 A1 * | 1/2006 | Greenberg et al. | 623/1.11 |
| 2007/0043425 A1 * | 2/2007 | Hartley et al. | 623/1.12 |
| 2007/0088424 A1 * | 4/2007 | Greenberg et al. | 623/1.12 |
| 2007/0219614 A1 | 9/2007 | Hartley | |
| 2008/0114438 A1 * | 5/2008 | Hartley et al. | 623/1.11 |
| 2008/0294234 A1 * | 11/2008 | Hartley et al. | 623/1.12 |

OTHER PUBLICATIONS

EPC Communication, EP 11 27 5167, communication dated May 11, 2015, 5pp.

* cited by examiner

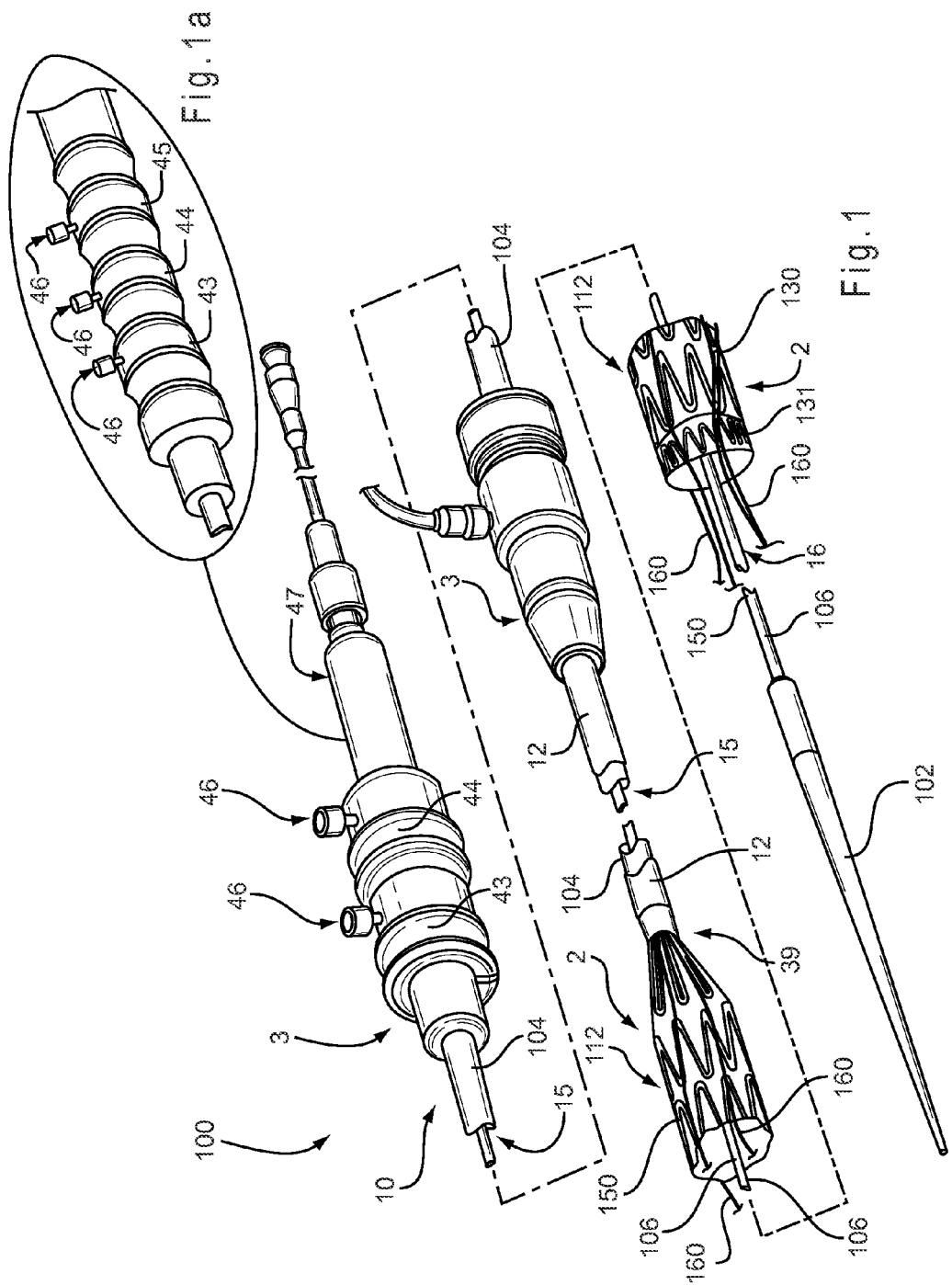

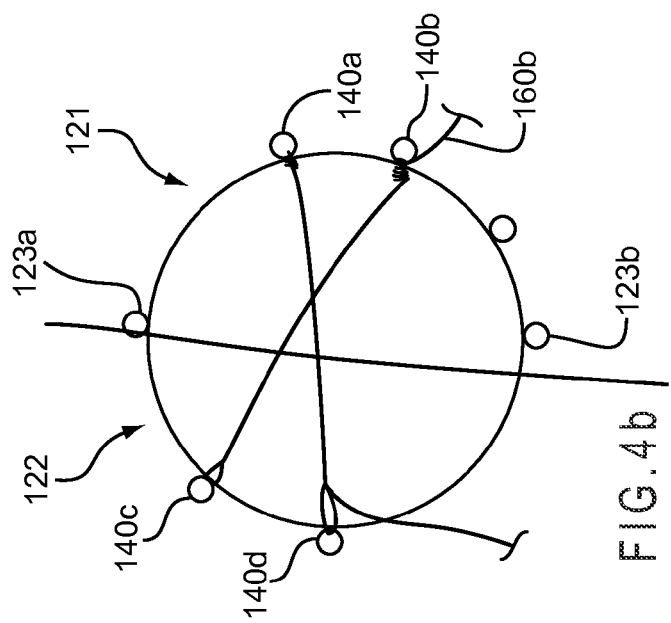
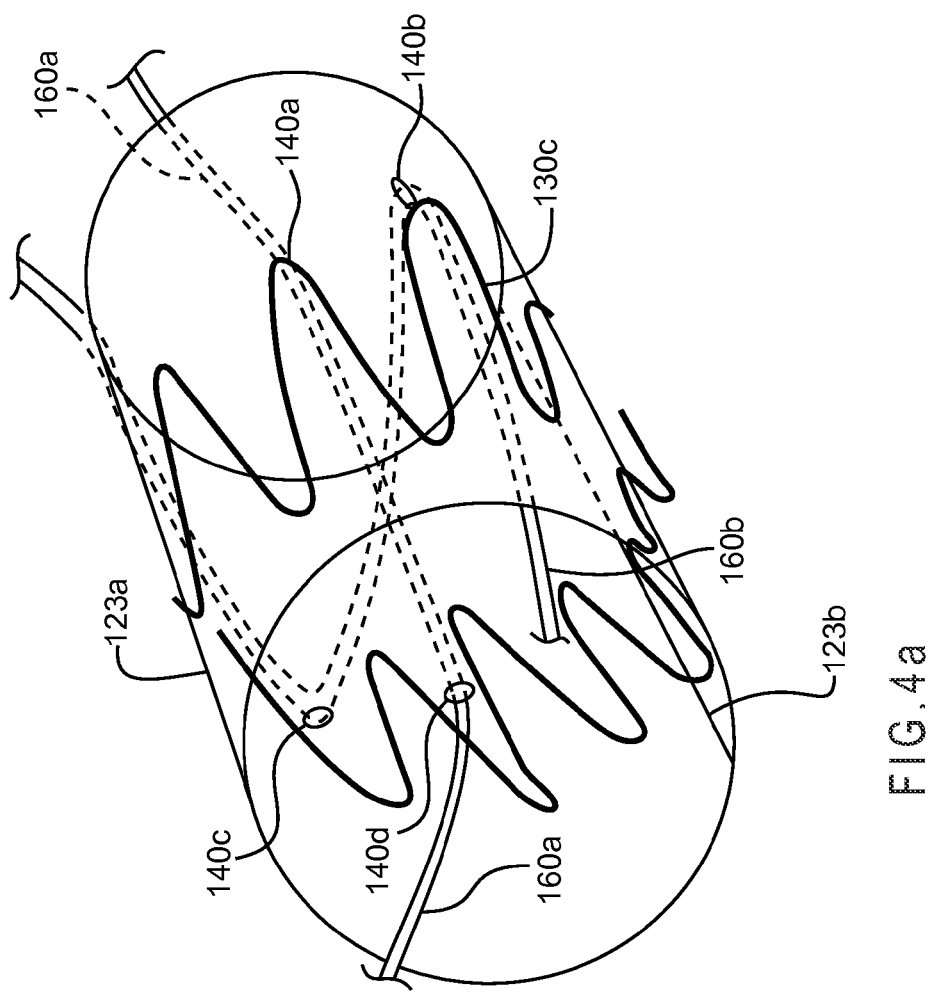

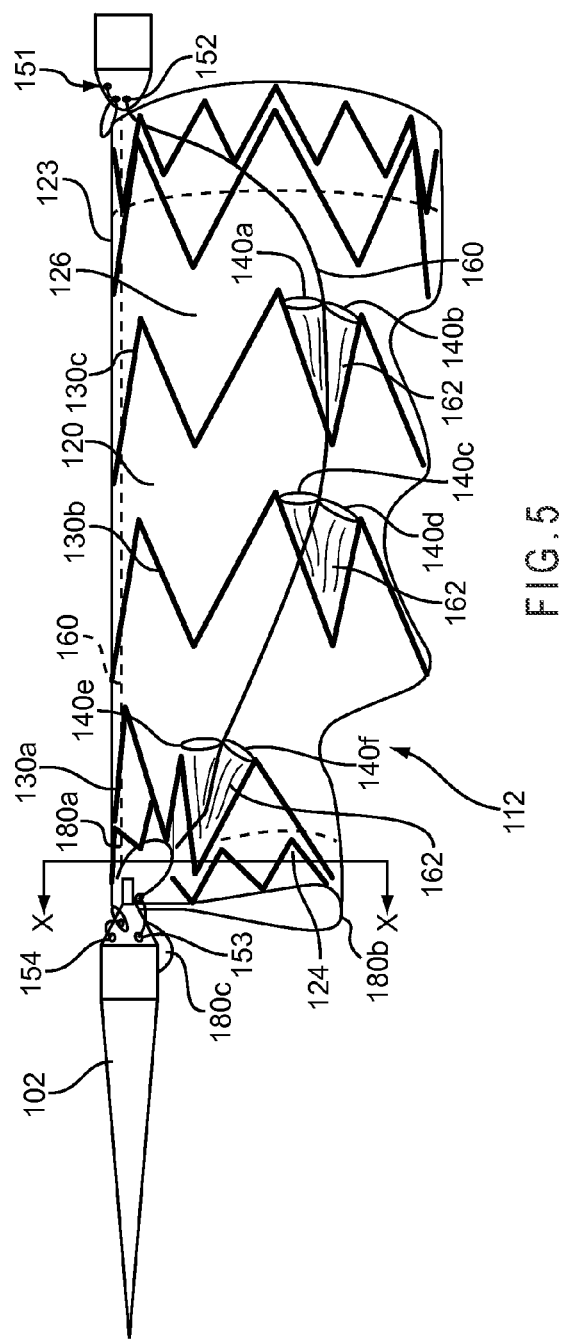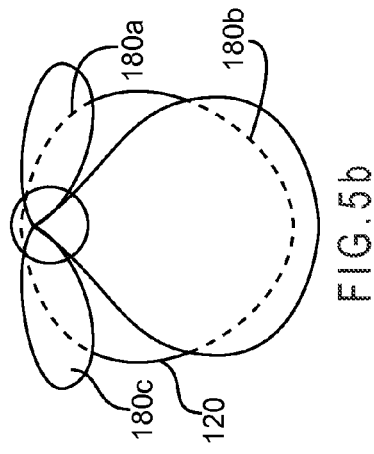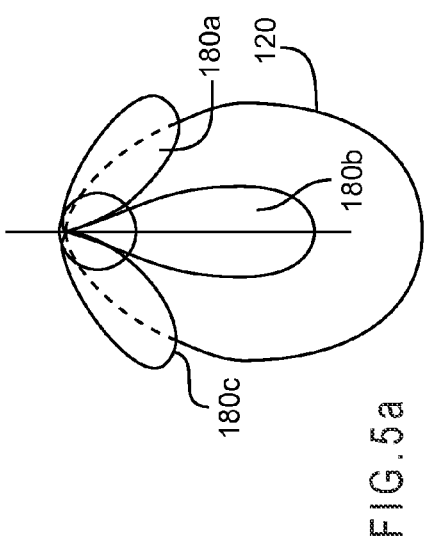

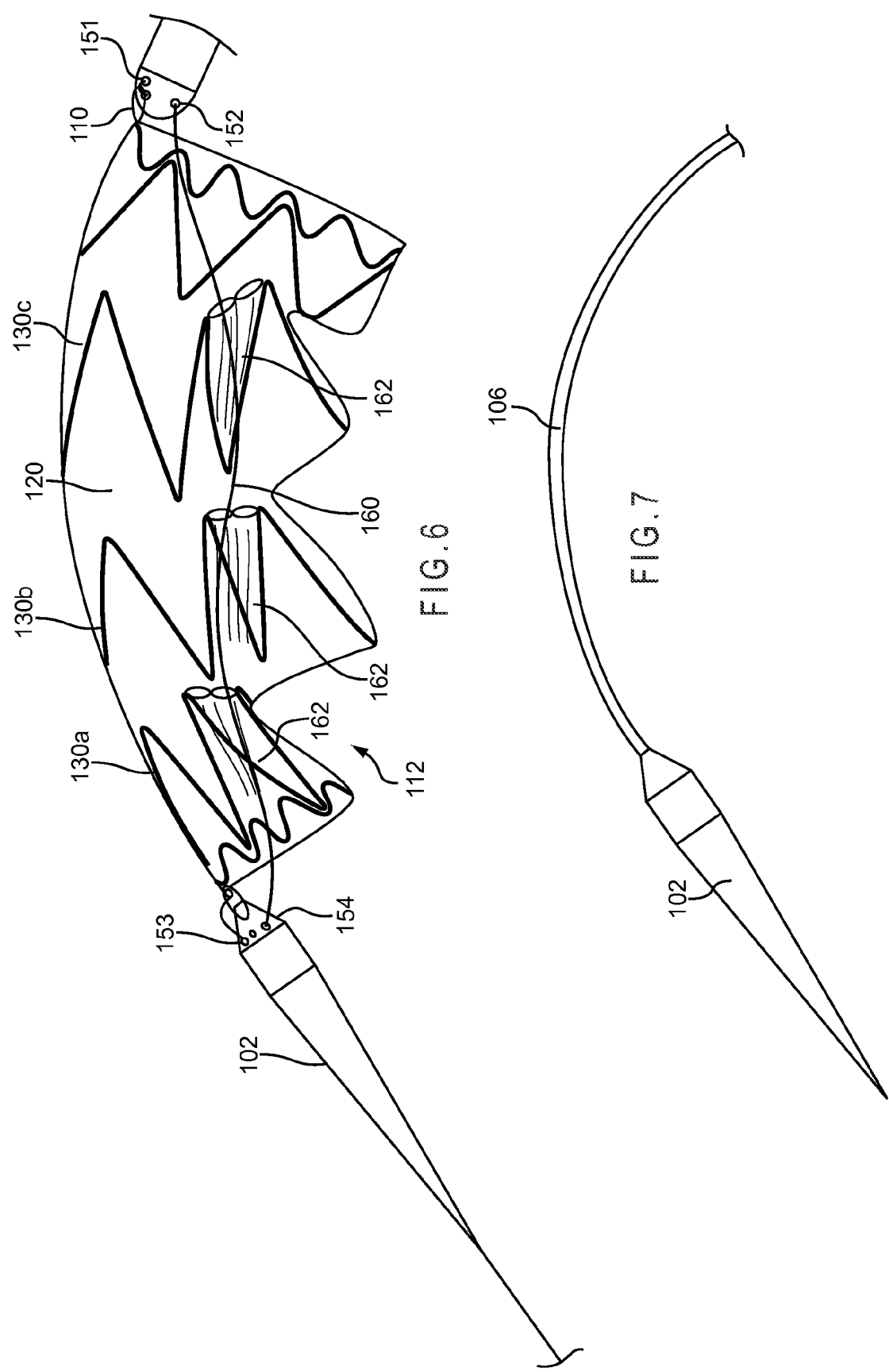

CONFORMABLE PROSTHESIS DELIVERY SYSTEM AND METHOD FOR DEPLOYMENT THEREOF

RELATED APPLICATIONS

The present application claims priority to U.S. Provisional Patent Application Ser. No. 61/429,081 filed Dec. 31, 2010, the entirety of which is hereby incorporated by reference.

BACKGROUND

1. Field of the Invention

This invention relates to medical devices and, in particular, to a delivery system for an endoluminal prosthesis and method of deploying the endoluminal prosthesis.

2. Description of the Art

Endovascular repair of thoracic pathologies is an effective, noninvasive treatment option that has gained tremendous popularity over the last ten years. However, challenging anatomy, such as highly curved or tortuous anatomy often leads to a non-ideal device deployment where the endovascular graft does not fully conform to the inner curvature of the vasculature. When deploying a stent-graft having a substantially cylindrical shape in a curved aorta or other vessel, there is a danger that the proximal end of the stent-graft, which is the end disposed nearer the heart, will not lie flat against the walls of the vessel. In this case, blood can flow underneath the edge of the graft. This problem is particularly common on the inner side of the curve of the aortic arch and is commonly referred to as "birds beaking." Generally the gap formed by "birds beaking" between the inner curve of the aortic wall and the proximal edge of the endovascular graft is in the range of 1-10 mm. Such gaps can and have led to device failures including: device migration, stent fatigue/fracture, endoleaks, etc. Accordingly, it has become apparent to the inventors that an improved system for delivering endoluminal prostheses, such as stent-grafts, is desirable.

BRIEF SUMMARY

Delivery systems for deploying endovascular prostheses, such as stent-grafts, are described which may be readily conformable to a patient's anatomy, for example, curved vessels such as the aortic arch, to allow for more accurate placement thereof. The embodiments may include any of the following aspects in various combinations and may also include any other aspect described below in the written description or in the attached drawings.

In one aspect, a delivery system for deploying a stent-graft may include: a cannula extending from a distal end to a proximal end; a stent-graft; a locking member extending from the distal end of the cannula to the proximal end of the cannula; and a first diameter reducing member.

The stent-graft may include a tubular graft extending from a proximal end to a distal end. The graft may include a proximal portion and first and second longitudinally extending sides disposed opposite each other. An intersection of the first and second halves may form a tangent line that extends longitudinally along a length of the graft. The locking member may be movable between a locked position, and a released position. When the locking member is in the locked position, the locking member may restrain a surface of the graft against the cannula along the tangent line, and a central axis of the cannula may be spaced away from a central axis of the graft.

The first diameter reducing member may extend from the distal end of the cannula and along a length of the graft. The first diameter reducing member may be slidably connected to a first portion of the graft that is disposed proximate the tangent line in the proximal portion and may be slidably connected to a second portion of the graft that is spaced circumferentially away from the tangent line in the proximal portion. The first diameter reducing member may have a restrained position and a released position. When the first diameter reducing member is in the restrained position, the second portion of the graft is drawn toward the first portion of the graft such that the proximal portion of the stent-graft has a reduced diameter configuration with at least two lobes that extend away from the tangent line and the cannula. When the first diameter reducing member is in the released position, the second portion is disposed away from the first portion of the graft, the proximal portion of the graft thereby having a substantially tubular configuration.

In another aspect, the delivery system may also include a second diameter reducing member extending from the distal end of the cannula and along a length of the graft. The second diameter reducing member may be slidably connected to a third portion of the graft that is disposed proximate the tangent line in the proximal portion and slidably connected to a fourth portion of the graft that is disposed in a position circumferentially spaced away from the tangent line in the proximal portion. The second diameter reducing member may have a restrained position and a released position. When the first and second diameter reducing members are in the restrained position, the fourth portion of the graft may be drawn toward the third portion of the graft such that the proximal portion of the stent-graft has a reduced diameter configuration with three lobes that extend away from the tangent line and the cannula. When the first and second diameter reducing members are in the released position, the second portion may be disposed away from the first portion of the graft, the proximal portion of the graft thereby having the substantially tubular configuration.

In another aspect, the stent-graft further may include a support structure attached to the graft. The support structure may include at least a first stent ring, where the first stent ring comprises a plurality of structural members connected by bends in an undulating pattern. A first diameter reducing connector may be attached to a first bend of the first stent ring, and a second diameter reducing connector may be attached to a second bend of the first stent ring. The first ring may be attached to an intermediate portion of the graft, and the first and second bends may be disposed on the first side of the graft and spaced circumferentially away from the tangent line.

In another aspect, the first diameter reducing member may extend from the first diameter reducing connector to the second diameter reducing connector in the intermediate portion of the graft. When the first diameter reducing member is in the restrained position, the first bend may be drawn circumferentially toward the second bend, thereby forming a first gather in the first side of the graft that decreases the diameter of the stent-graft in the intermediate portion.

A method of repairing a damaged or diseased vessel may include: providing a delivery system as described above; restraining a surface of the graft against the cannula along the tangent line and displacing a central axis of the cannula away from a central axis of the graft by moving the locking member to the locked configuration; forming a reduced diameter configuration in the proximal portion of the stent-graft having at least two lobes by moving the first diameter reducing member to the restrained position and draw the second portion of the graft toward the first portion of the graft; advancing the delivery system into a curved lumen; and moving the diameter reducing members to the released position, whereby the proximal portion of the stent graft is released from the reduced diameter configuration and the proximal portion of the stent-graft assumes a substantially tubular configuration.

The foregoing paragraphs have been provided by way of general introduction, and are not intended to limit the scope of the following claims.

BRIEF DESCRIPTION OF THE DRAWINGS

The embodiments described below may be more fully understood by reading the following description in conjunction with the drawings, in which:

FIG. 1 is a perspective view of a delivery system for an endoluminal prosthesis;

FIG. 1a is a close-up view of an alternative embodiment of a control handle arrangement of the delivery system of FIG. 1;

FIG. 3a is a cross-sectional view of the stent-graft of FIG. 3 taken long the line Y-Y;

FIG. 4a is a perspective view of a portion of a stent-graft illustrating an alternative embodiment to the embodiment shown in FIG. 4;

FIG. 4b is an end view of the embodiment of FIG. 4a;

FIG. 5 is a side perspective view of the delivery system of FIG. 1 illustrating the diameter reducing member in a tightened configuration;

FIG. 5a is a front cross-sectional view taken along the line X-X of the graft of FIG. 5 in a three lobed reduced diameter configuration;

FIG. 5b is an alternative three lobed configuration of the graft of FIG. 5a;

FIG. 6 is a side view of the endoluminal prosthesis of FIG. 5 mounted on a delivery system having a curved cannula;

FIG. 7 is a side view of the delivery system of FIG. 6 illustrating the curved cannula;

DETAILED DESCRIPTION OF THE DRAWINGS AND THE PRESENTLY PREFERRED EMBODIMENTS

Figure 1B:
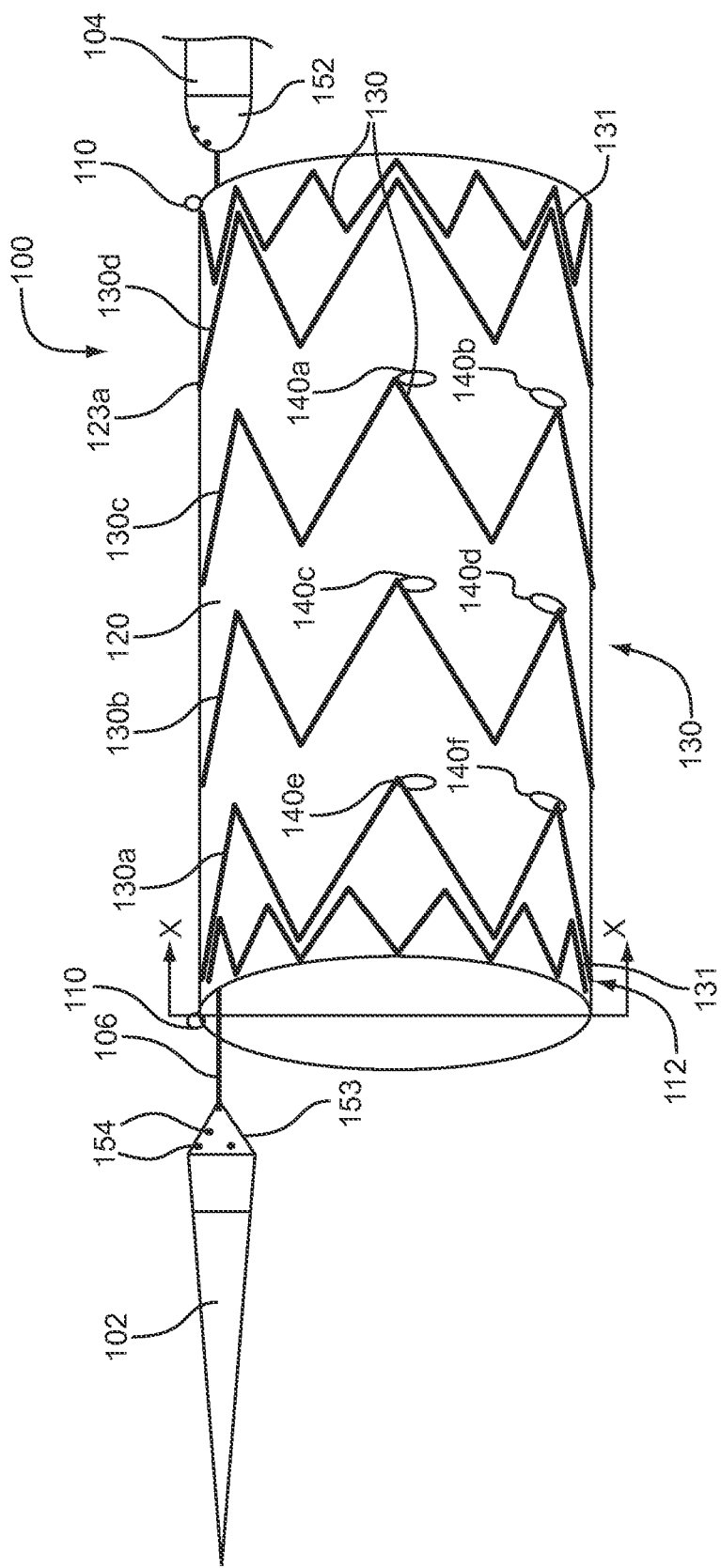
FIG. 1b is a side perspective view of the delivery system of FIG. 1.

Throughout this specification, like reference numbers refer to like elements.

The terms "distal" and "distally" refer to a position, direction, or orientation that is generally away from the heart. The terms "proximal" and "proximally" refer to a position, direction, or orientation that is generally toward, or closer to the heart.

The terms "endoluminal device" or "endoluminal prosthesis" refer to or describe objects that can be placed inside a vessel, a lumen, or a body passageway in a human or animal body. A lumen, vessel, or a body passageway can be a naturally occurring lumen or a lumen created by surgical intervention. As used in this specification, the terms "lumen" or "body passageway" are intended to have a broad meaning and encompasses any duct (e.g., natural or iatrogenic) within the human body and can include blood vessels, respiratory ducts, gastrointestinal ducts, and the like. Thus, "Endoluminal device" or "endoluminal prosthesis" describes devices that can be placed inside one of these lumens.

The term "fenestration" refers to an opening in a generally fluid impermeable structure through which fluid can pass.

The term "stent" means any device or structure that adds rigidity, expansion force or support to a prosthesis or body lumen. A stent is used to obtain and/or maintain a patency of the body passageway while maintaining the integrity of the passageway. In addition, a stent may be used to form a fluid seal against the body lumen. The stent may be coated with a polymeric material, for example, by immersion in liquid polymer or any other method known to one of skill in the art. The stent may be located on the exterior of a prosthesis, an interior of the prosthesis, or both. A stent may be self-expanding, balloon-expandable or may have characteristics of both.

The term "graft" or "graft material" may comprise a biocompatible synthetic or biological material. Examples of suitable synthetic materials include fabrics, woven and non-woven materials, and porous and non-porous sheet materials. One exemplary synthetic graft material includes a woven polyester having a twill weave and a porosity of about 350 ml/min/cm2, and is available from VASCUTEK® Ltd., Renfrewshire, Scotland, UK. Other synthetic graft materials include biocompatible materials such as polyester, polytetrafluoroethylene (PTFE), polyurethane, and the like. Examples of suitable biological materials include, for example, pericardial tissue and extracellular matrix materials such as SIS.

Examples of suitable graft materials are described in U.S. Pat. Nos. 4,502,159, 4,675,361, 4,861,830, 4,902,508, 5,017, 664, 5,733,337, 6,206,931, 6,358,284, 6,379,710, 6,666,892, 6,752,826, and 6,939,377, in U.S. Patent Application Publication Nos. 2002/0187288 A1 and 2003/0149471 A1, and in PCT Published Patent Application No. WO 98/22158, which are each incorporated by reference herein in their entirety.

The term "vessel" refers to a tube, cavity, duct, or canal in which fluid may be contained and conveyed or circulated. A body vessel (as opposed to a prosthetic vessel) is a vessel that exists naturally, or is formed naturally in the body. Examples of body vessels include, but are not limited to, blood vessels such as the aorta and the femoral artery, the esophagus, the trachea, the ureter, the bile duct, and the like. Examples of prosthetic vessels include, but are not limited to, stents, grafts, stent-grafts, venous or aortal valves, vena cava filters, and the like.

The term "lumen" describes a space within a vessel in which fluid may be contained, conveyed, and/or circulated. The term "endoluminal" means within a lumen, and can refer to objects that are found or that can be placed within a lumen, or methods or processes that occur within a lumen. An "endoluminal prosthesis" is a prosthesis that is found or that can be placed within a lumen. Examples of endoluminal prostheses include, but are not limited to, stents, grafts, stent-grafts, venous or aortal valves, vena cava filters, and the like. An endoluminal prosthesis may be generally tubular and comprise one or more lumens. Examples of tubular prostheses include, but are not limited to, straight, curved, branched, and bifurcated prostheses.

The term "clock" or "clocked" refers to an orientation that is circumferentially spaced away from a fixed reference point in a manner similar to the numbers on an analog clock, which are circumferentially spaced away from each other. For example, as shown in FIG. 2, the point 123d is "clocked"

circumferentially away from the tangent line 123a in the clockwise direction. Similarly, the point 123c is clocked circumferentially away from the tangent line 123a in the counterclockwise direction.

Referring now to the figures, FIG. 1 illustrates an embodiment of a delivery system 100 for delivering and deploying a medical device, such as the stent-graft 112 shown in FIGS. 1b-6. The delivery system 100 may include a delivery catheter 10 and a sheath 12. In operation, the delivery catheter 10 and the sheath 12 are configured to selectively retain and release the stent-graft 112. The delivery catheter 10 has a proximal end and a distal end.

A dilator head, also referred to as a nose cone 102, is disposed at the proximal end of the delivery catheter 10. The nose cone 102 is tapered in the distal direction to provide for a smooth, atraumatic transition from a guidewire over which the delivery system 100 is advanced into a body lumen or cavity. A guidewire lumen 15 extends longitudinally through the delivery catheter 10 between the proximal and distal ends. The delivery catheter 10 is configured to receive a guidewire through the guidewire lumen 15. The delivery catheter 10 may also include a prosthesis receiving portion 16, as shown in FIG. 1. The receiving portion 16 may be disposed at a proximal portion of the delivery catheter 10 and is configured to receive the stent-graft 112 in a radially compressed configuration. As shown in FIG. 1, the receiving portion 16 may include a longitudinally extending cannula 106 having a uniform external diameter along its length.

The sheath 12 may be manipulated to selectively deliver and deploy the stent-graft 112 in the body lumen. As shown in FIG. 1, a catheter 104 having a longitudinally uniform external diameter may be included in the delivery system 100. The diameter of the catheter 104 may be larger than the diameter of the cannula 106. A proximal-facing annular abutment surface may be disposed at the transition between the cannula 106 and the catheter 104. The annular abutment surface faces the distal end of the stent-graft 112 and is configured to contact the distal end of the stent-graft 112 during deployment, thereby holding the stent-graft 112 in place at a treatment site within a body lumen or cavity when the sheath 12 is withdrawn in the distal direction.

The sheath 12 may include an elongate tubular body having a wall thickness and a proximal and distal end. The sheath 12 may be formed as a composite of two or more layers of the same or different materials that are laminated or otherwise mechanically bonded together. An inner surface of sheath 12 defines a lumen extending along a longitudinal axis thereof. The lumen may have a generally constant diameter along its length. The sheath 12 extends distally from the delivery section 2 to the user manipulation section 3, which includes a control handle 47. The delivery catheter 10 is slideably disposed within the lumen. The sheath 12 may slideably cover and restrain the stent-graft 112 onto the cannula 106 in a radially compressed configuration in which the diameter of the stent-graft 112 is reduced as compared to its unrestrained state. The nose cone 102 may have a recessed portion disposed at its distal end that is shaped to receive the proximal end of the sheath 12 and form a generally smooth transition therebetween so as to prevent trauma to the body lumen or cavity as the delivery catheter 10 is advanced into the patient for delivery and deployment of the stent-graft 112. The distal end of the sheath 12 may be configured to remain outside of the body during the procedure, in which case the sheath 12 may be directly manipulated through the control handle 47 by the operator to deploy the stent-graft 112.

The sheath 12 may have a length, as shown in FIG. 1, that is greater than the length of the stent-graft 112. For example, the sheath 12 may have a length that is two or more times greater than the length of the stent-graft 112. Alternatively, the sheath 12 may have a length that is generally equal to or only slightly greater than the length of the stent-graft 112. The sheath 12 may have a uniform internal diameter. The internal diameter may be substantially equal to the external diameter of the catheter 104 such that the inner surface of the sheath 12 slideably engages the delivery catheter 10.

The sheath 12 may be made of any suitable biocompatible material, for example PTFE, nylon, or polyethylene. The sheath 12 may optionally include a flat wire coil or braid disposed between or incorporated into the one or more layers of material to provide the sheath 12 with increased pushability and kink-resistance as the sheath 12 is advanced through the body lumen or cavity, as discussed in U.S. Pat. No. 5,380,304 and U.S. Published Patent Application No. 2001/0034514 A1, which are incorporated herein by reference in their entirety.

As shown in FIGS. 1 and 1b, the stent-graft 112 may include a plurality of self-expanding stents 130 and self-expanding sealing stents 131. Stents having self-expanding characteristics may be made of stainless steel, materials with elastic memory properties, such as NITINOL, or any other suitable material. A suitable self-expanding stent includes Z-STENTS®, which are available from Cook Incorporated, Bloomington, Ind., USA. When the sheath 12 is removed, the compressed stents 130 and sealing stents 131 cause the stent-graft 112 to expand. The stent-graft 112 also may include an anchor, such as an exposed strut or barb, for anchoring the stent-graft 112 in the body lumen. As shown in FIGS. 1 and 1b, the stents 130 and sealing stents 131 may be formed from a single or multiple wires having a zigzag shape and may comprise barbs, or other anchoring mechanisms that extend from the stent. When the stents 130 and sealing stents 131 are released, the barbs or other anchoring mechanisms engage the surrounding lumen and help prevent migration of the stent-graft 112 after implantation in the body lumen or cavity.

The stents 130 may cover and/or may be at least partially covered by a graft material. Various graft materials and configurations may be used. Suitable graft configurations include, but are not limited to films, coatings, sheets of biocompatible fabrics, non-woven materials and porous materials. Examples of suitable graft materials include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; polyurethanes, including polyetherurethanes, polyurethane ureas, polyetherurethane ureas, polyurethanes containing carbonate linkages and polyurethanes containing siloxane segments; and bioremodelable materials, such as small intestine submucosa ("SIS").

In operation, when the sheath 12 is withdrawn distally, the operator applies pressure to the delivery catheter 10 in the proximal direction through the catheter 104. As the sheath 12 is withdrawn, the distal end of the stent-graft 112 contacts the abutment surface, which exerts a reaction force on the stent-graft 112 that prevents the stent-graft from moving distally with the sheath 12.

The delivery system 100 may also include a distal end deployment control mechanism 39, as shown in FIG. 1. The distal end deployment control mechanism 39 releasably retains the distal end of the stent-graft 112. The distal end deployment control mechanism 39 may include one or more trigger wires that releasably couple the distal end of the stent-graft 112 to the delivery catheter 10. The distal end of the trigger wire for the distal end deployment control mechanism 39 may be attached to the release device 44. A proximal end control release mechanism may include one or more diameter reducing members 160 and a locking member 150, all of which may be formed as trigger wires or the like, as described in detail below in connection with FIGS. 1b-6. The diameter reducing member(s) 160 and the locking member 150 may extend distally to the external manipulation section 3 shown in FIG. 1, where they are coupled to one or more of the release devices 43, 44. The release devices 43, 44 may be configured to selectively decouple the proximal and distal ends of the stent-graft 112 from the delivery catheter 10, respectively. For example, in one embodiment, the distal ends of two diameter reducing members 160 may be attached to the release device 44, and the distal end of the locking member 150 may be attached to the release device 43. In this embodiment, the delivery system 100 may include a third, separate release device 45 attached to the distal end of the trigger wire for the distal end deployment control mechanism 39 to allow selective release and retention of the trigger wire of the distal end deployment control mechanism 39 independently of the diameter reducing members 160 and the locking member 150, as shown in FIG. 1a. The third release device may 45 be disposed in a slidably movable arrangement on the control handle 47, and may have a similar or identical structure to the release devices 43, 44 pictured in FIG. 1.

In operation, the release device 45 is first unlocked by loosening a set screw or other locking device 46 and then the release device 45 is withdrawn distally, which pulls the trigger wire of the distal end deployment control mechanism 39 in the distal direction and releases the distal end of the stent-graft 112. Next, the locking device 46 is loosened and the release device 44 is withdrawn distally, which pulls the diameter reducing members 160 in the distal direction and causes the diameter reducing member 160 to disengage from the stent-graft 112, thereby allowing the stent-graft to be released. Following withdrawal of the diameter reducing members 160, the release device 43 can then be unlocked by loosening a separate locking device 46 and the locking member 150 can be released by withdrawing the release device 43 in the distal direction. In one alternative embodiment, the distal end of one of the diameter reducing members 160 may be attached to an additional release device that is separate from the release devices 43, 44, 45. This additional release device may be slidably attached to the control handle 47 and disposed between the release devices 44 and 45. In this embodiment, the distal end of the other diameter reducing member 160 is attached to the release device 44 and the distal end of the locking member 150 is attached to the release device 43. Because each of the diameter reducing members 160 and the locking member 150 are attached to separate, independent release devices, the diameter reducing members 160 and the locking member 150 can be withdrawn from the stent-graft 112 independently of one another.

Returning to the embodiment of FIG. 1, the trigger wire of the distal end deployment control mechanism 39 may be attached to the release device 44 and the diameter reducing members 160 and the locking member 150 may all be attached to the same release device 43. In this embodiment, the release device 44 is first unlocked by loosening a set screw or other locking device 46 and then the release device 44 is withdrawn distally, which pulls the trigger wire of the distal end deployment control mechanism 39 in the distal direction and releases the distal end of the stent-graft 112. Next, the locking device 46 is loosened and the release device 43 is withdrawn distally, which pulls the diameter reducing members 160 and the locking member 150 simultaneously in the distal direction and causes the diameter reducing members 160 and the locking member 150 to disengage from the stent-graft 112, thereby allowing the stent-graft to be released.

FIG. 1b illustrates a detailed view of the delivery system 100 with the sheath 12 and distal end deployment control mechanism 39 removed to better illustrate the configuration of the stent-graft 112. As shown in FIG. 1b, the nose cone 102 is attached to a proximal end of a cannula 106, and the distal end of the cannula 106 is attached to the catheter 104. The stent-graft 112 is disposed about the cannula 106 in a non-co-axial, tangential relationship relative to a surface of the stent-graft 112 where a central axis of the stent-graft 112 is spaced away from a central axis of the cannula 106. While the cannula 106 is shown in FIG. 1 as having a straight configuration, it may also have a curved configuration, as shown in FIG. 7, that substantially approximates the curvature of a portion of the body lumen in which the stent-graft 112 is to be deployed, for example, the aortic arch. As will be described in detail below and shown in FIG. 6, because the stent-graft 112 is restrained against the curved cannula 106, the stent-graft assumes a curved configuration prior to deployment that also approximates the curvature of the target site of the vessel to increase conformity to the vessel's shape and increase placement accuracy.

Returning to FIG. 1b, the stent-graft 112 includes a tubular graft material 120 attached to a support frame or structure comprising a plurality of stents 130 and sealing stents 131 having an undulating or zigzag configuration. The stents 130 and sealing stents 131 may comprise a plurality of structural members connected together at their ends by bends. The stents 130 and sealing stents 131 may be formed from a single wire made of Nitinol, stainless steel, polymers, or other materials having elastic or super elastic properties. Alternatively, the stents 130, 131 may be cut from a cannula or the like. As shown in FIG. 1b, the sealing stents 131 may have a shorter longitudinal length and a higher "frequency" of bends than the stents 130. This higher frequency of bends provides a more even distribution of force along the surface of the graft 120 at the proximal and distal ends. The sealing stents 131 may be attached to the graft 120 along an inner surface thereof to force the graft 120 directly against the vessel wall to provide better apposition against the vessel wall and prevent fluid from passing between the stent-graft 112 and the vessel wall in the deployed state. In contrast, the stents 130 may have a greater overall longitudinal length and a smaller amplitude, and may be made from a thicker material in order to provide a stronger radial force (in a radially outward direction) that is capable of holding the stent-graft 112 in the open configuration upon deployment and maintaining patency of the lumen extending through the stent-graft 112. As shown in FIGS. 1b-6, the stents 130 and the sealing stents 131 may comprise individual, discreet stents 130a, 130b, 130c, 130d, etc., with each stent/sealing stent having a ring-like shape (e.g. a "stent ring"). The stents 130a, 130b, 130c, and 130d may be spaced longitudinally apart from one another in intervals along the length of the graft 120. In another embodiment, the stent or stent rings may be connected together to form a single monolithic structure that extends and wraps around the graft 120 in a helical form along a portion or an entire length thereof.

Figure 2A:
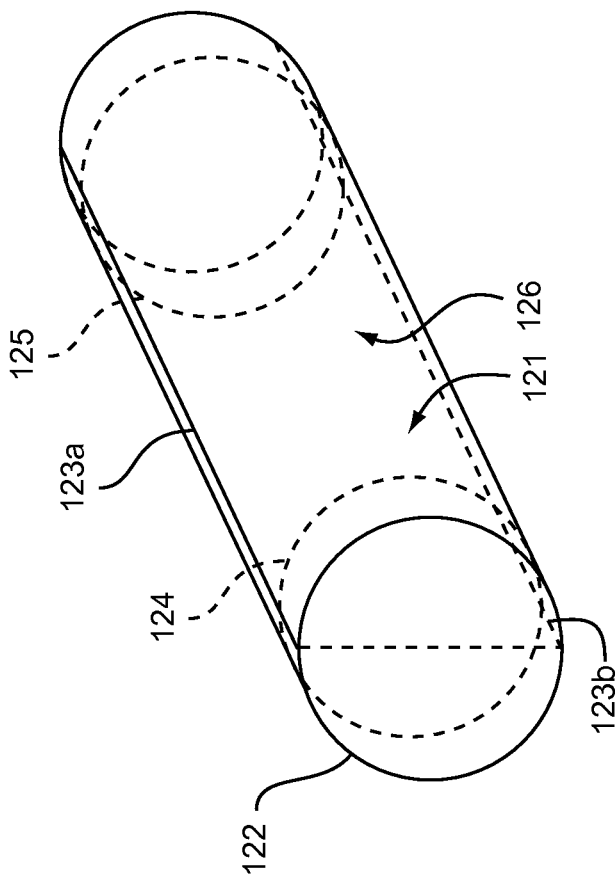
FIG. 2a is a perspective view of the graft of FIG. 2.
Figure 2:
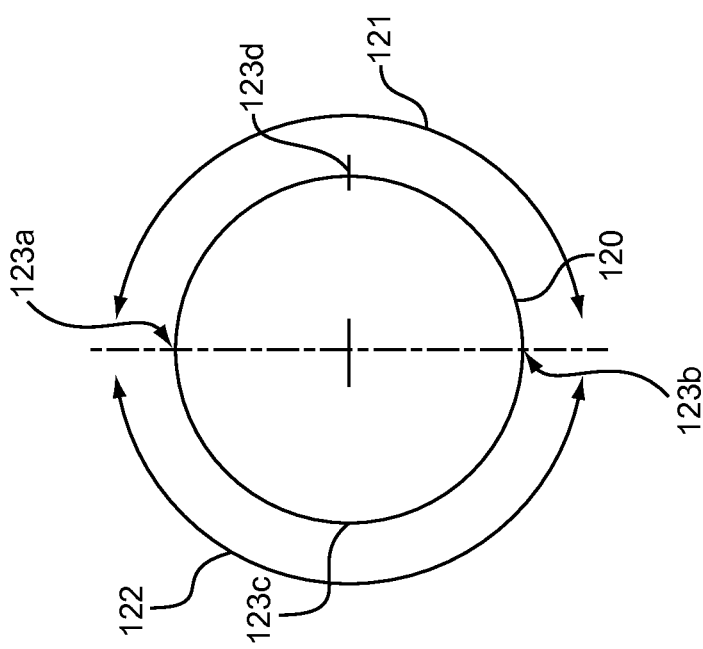
FIG. 2 is a front cross sectional view of a graft taken along the line X-X of FIG. 1b.

Turning to FIG. 2a, the graft 120 may be comprised of, or divided into two circumferential sides or halves 121, 122. As shown in FIG. 2a, the halves 121, 122 may have a half-cylindrical, longitudinally extending shape. The halves 121, 122 may meet along one edge at a tangent line 123a and along another edge at a tangent line 123b, with the tangent lines 123a, 123b extending in a substantially straight line along the length of the graft 120 from the proximal to the distal end thereof. The graft 120 may also be divided into three longitudinal portions: a proximal portion 124 including the proximal end of graft 120, an intermediate portion 126, and a distal portion 125 including the distal end of the graft 120. Note that the proximal portion 124, the intermediate portion 126, and the distal portion 125 refer generally to longitudinal regions of the graft 120.

Returning to FIG. 1b, a locking member connector 110 is attached to the proximal and distal ends of the stent-graft 112 at or near the tangent line 123a. A plurality of diameter reducing connectors 140, which may be formed by sutures, wire loops or the like, are attached to one or more bends of the stents 130, 131 and may also be attached to the graft 120. In one embodiment, the diameter reducing connectors 140 may be attached to bends of the stent ring 130a, which is disposed longitudinally adjacent to the proximal sealing stent 131. In this embodiment, the diameter reducing connectors 140 are also attached to bends of the stents 130b, 130c, which are disposed longitudinally adjacent to, and spaced apart from the stent 130a moving in the distal direction along the length of the graft 120. Specifically, the diameter reducing connectors 140e and 140f are attached to circumferentially adjacent bends aligned at the distal end of the stent 130a. Similarly, the diameter reducing connectors 140c and 140d are attached to circumferentially adjacent bends aligned along the distal end of the stent 130b, and the diameter reducing connectors 140a and 140b are attached to circumferentially adjacent bends aligned along the distal end of the stent 130c. While no diameter reducing connectors are shown as being attached to the distal most stent 130d, it should be understood that diameter reducing ties 140 may also be attached to bends of the stent 130d. Additionally, while only two diameter reducing connectors 140 are shown as being attached to each stent 130, more diameter reducing ties 140 may be attached to bends disposed at either the proximal or distal end of each or any of the stents 130.

Note that while only one side of the stent-graft 112 corresponding to the half 121 is shown in FIGS. 1b-6, the stent-graft 112 may be constructed in a mirror image configuration about the tangent line 123a. Thus, diameter reducing connectors 140 may also be attached to the stent rings 130a, 130b, and 130c at bends disposed at the same circumferential position or substantially the same circumferential position on the half 122, as the half 121 shown in, for example, FIG. 3a. As shown in FIG. 3a, the diameter reducing connectors 140 are circumferentially clocked away from the tangent line 123a in the counter clockwise direction for the half 122 and in the clockwise direction for the half 121. Preferably, the diameter reducing connectors 140 are attached to bends of the stents 130a, 130b, and 130c, which are clocked away from the tangent line 123a by between 90 and 180 degrees on the first and second sides 121, 122. As shown in FIGS. 5-5b and described in detail below, in one embodiment, the diameter reducing connectors 140 may be attached to bends of the stents 130 that are clocked away from the tangent line 123a in the counterclockwise direction on side 121 and in the clockwise direction on side 122 such that, when the diameter reducing connectors 140 are drawn toward each other by a diameter reducing member 160, a gather 162 (see e.g., FIG. 5) is formed in the graft 120 that is clocked roughly 120 degrees away from the tangent line 123a on one or both of the first and second sides 121, 122.

Figure 3:
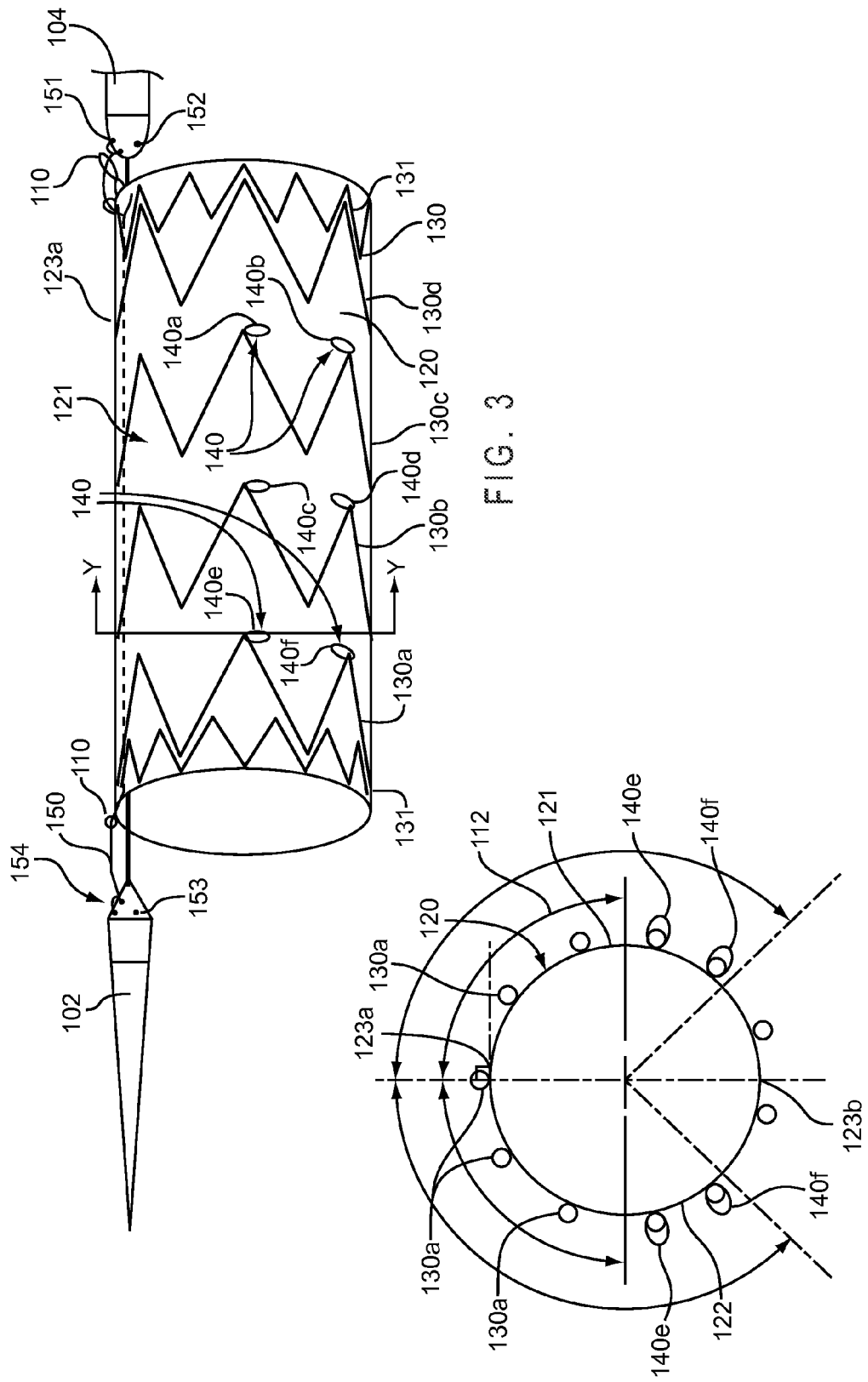
FIG. 3 is a side perspective view of the delivery system of FIG. 1 including a locking member.

Turning to FIG. 3, a locking member 150 may extend from the release device 43, through the catheter 104 and out of an aperture 151 disposed at the proximal end of the catheter 104. The locking member 150 may be a suture, a wire made from a titanium alloy, such as Nitinol, or other flexible elongate mono or multifilament member of suitable tensile strength.

As shown in FIG. 3, the locking member 150 may extend from the aperture 151, through the distal locking member connector 110, along either the interior or exterior of the graft 120, through the proximal locking member connector 110, and into the nose cone 102 through an aperture 154. The proximal end of the locking member 150 may be frictionally attached to the nose cone 102 by an elastomer or other friction locking mechanism housed within the aperture 154. During assembly, the proximal end of the locking member 150 is held stationary while the distal end of the locking member 150 is pulled in the distal direction and fixed to the release device 43 in a tightened configuration. As the locking member 150 tightens, the locking member 150 pulls the proximal and distal locking member connectors 110 toward the cannula 106 and into a locked configuration in which the locking member 150 is disposed substantially against or adjacent to either the inner or outer surface of the stent-graft 112 (depending on whether the locking member 150 is disposed on the inside or outside of the stent-graft 112) in a region of the graft 120 that substantially corresponds to the tangent line 123a. In this locked configuration, the locking member 150 compressively restrains the stent-graft 112 against the cannula 106 in a non-coaxial arrangement. For example, the cannula 106 may abut the tangent line 123a on the surface of the stent-graft 112.

Figure 4:
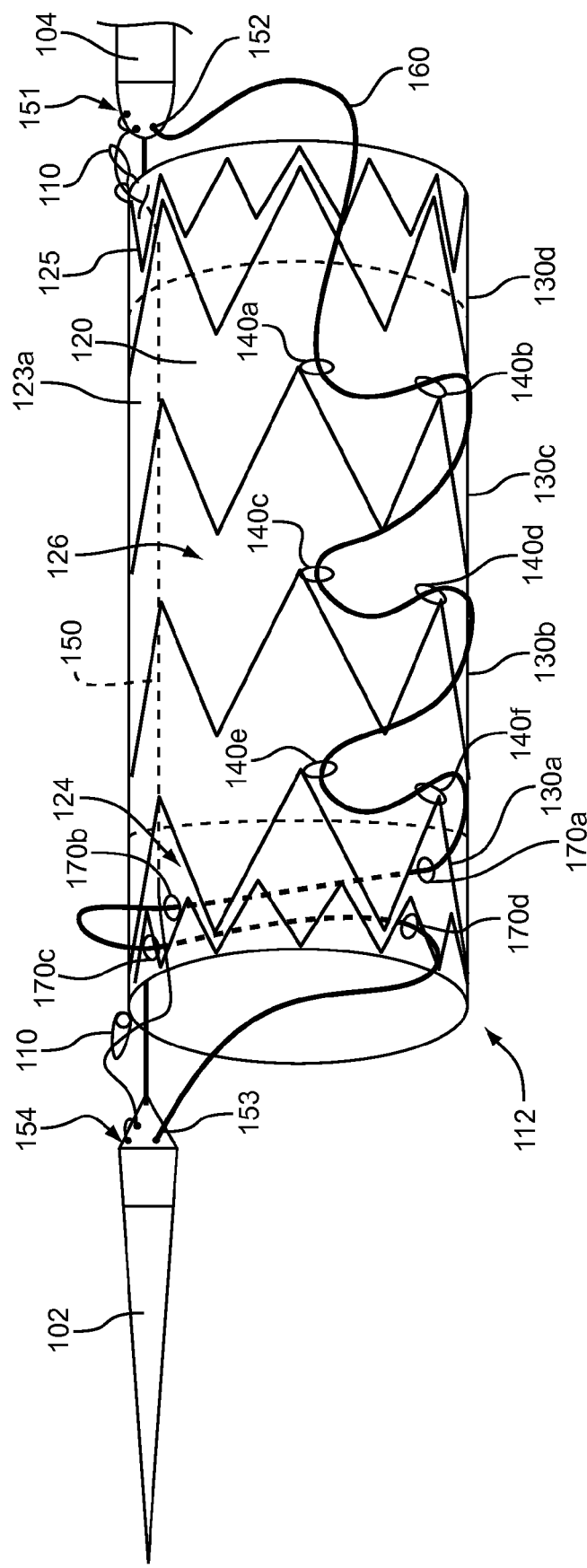
FIG. 4 is a side perspective view of the delivery system of FIG. 1 including a diameter reducing member.

As shown in FIG. 4, a first diameter reducing member 160 extends from the release device 44, through the catheter 104 and out of an aperture 152 disposed at the proximal end of the catheter 104. The diameter reducing member 160 may be formed from a suture, a wire made from a titanium alloy, such as Nitinol, or other flexible elongate mono or multifilament member of suitable tensile strength. From the catheter 104, the diameter reducing member 160 extends along either an internal or external surface of the stent-graft 112. In embodiments in which the diameter reducing member 160 extends along an internal surface of the stent-graft 112, the diameter reducing member 160 may initially extend from the aperture 152, along the internal surface of the stent-graft 112, and through the diameter reducing connector 140a. The diameter reducing member 160 may then extend through the diameter reducing connector 140b of the stent 130c in a circumferentially downward direction in FIG. 4. Next the diameter reducing member 160 may extend upward in FIG. 4 to the connector 140c of the stent 130b, and then downward to the connector 140d. This same pattern may be continued for the diameter reducing connectors 140e and 140f of the stent 130a. The diameter reducing member 160 may then extend proximally along the graft 120 and through the fenestrations 170a-d disposed in the proximal portion 124 of the graft 120. Specifically, the diameter reducing member 160 may extend through the fenestration 170a into the exterior of the stent-graft 112, where it continues to the aperture 170b disposed at or near the tangent line 123 and to the inside of the graft 120. The diameter reducing member 160 may then extend through the fenestration 170c back to the exterior of the stent-graft 112 and through the fenestration 170d, which may be disposed toward the bottom of the stent-graft 112 in FIG. 4. The diameter reducing member 160 then extends into the nose cone 102 through an aperture 153 where it is frictionally locked in place by an elastomer or other friction locking mechanism housed within the aperture 153. Similarly, a second diameter reducing member 160 is disposed on the opposite side of the graft 120 (side 122) in a similar, mirrored configuration, as described above in connection with FIG. 4.

In embodiments in which the diameter reducing member 160 extends along an external surface of the stent-graft 112, the diameter reducing member may 160 initially extend from the aperture 152, along the external surface of the stent-graft 112, and through the diameter reducing connector 140a. The diameter reducing member 160 may then extend through the diameter reducing connector 140b of the stent 130c in a circumferentially downward direction in FIG. 4. Next the diameter reducing member 160 may extend upward in FIG. 4 to the connector 140c of the stent 130b, and then downward to the connector 140d. This same pattern may be continued for the diameter reducing connectors 140e and 140f of the stent 130a. The diameter reducing member 160 may then extend proximally along the graft 120 and through the fenestrations 170a-d, which are disposed in the proximal portion 124 of the graft 120. Specifically, the diameter reducing member 160 may extend through the fenestration 170a into the interior of the stent-graft 112 where it continues to the aperture 170b that is disposed at or near the tangent line 123a, and to the outside of the graft 120. The diameter reducing member 160 may then extend through the fenestration 170c, back to the interior of the stent-graft 112 and through the fenestration 170d, which is disposed toward the bottom of the stent-graft 112 in FIG. 4. The diameter reducing member 160 may then extend into the nose cone 102 through an aperture 153 where it is frictionally locked in place by an elastomer or other friction locking mechanism housed within the aperture 153. Similarly, a second diameter reducing member 160 may be disposed on the opposite side of the graft 120 in a similar, mirrored configuration as described above in connection with FIG. 4.

It should be noted that the fenestrations 170a-d may be formed simply by piercing the graft material by a needle or a sharp end of the diameter reducing member 160 themselves. Alternatively, the fenestrations 170a-d may be formed as permanent openings or apertures that are woven or otherwise cut or formed into the graft 120. In an alternative embodiment, the diameter reducing members 160 may be slidably attached to the proximal portion 124 of the stent-graft 112 through connecting members, such as loops of suture or wire disposed at substantially the same positions as the fenestrations 170a-d.

In another embodiment shown in FIGS. 4a and 4b, a diameter reducing member 160a may extend along the internal surface of the stent-graft 112 from the catheter 104, through the diameter reducing connector 140a, which is attached to a bend of the stent 130c on the first side 121 of the graft 120, and to the diameter reducing connector 140d, which is disposed on the second side 122. Similarly, the diameter reducing member 160b may extend along the internal surface of the stent-graft 112 from the catheter 104, through the diameter reducing connector 140c on the second side 122 of the graft 120, and to the diameter reducing connector 140b on the first side of the graft 120. The diameter reducing members 160a and 160b then extend through the diameter reducing connectors 140 on the stents 130a and 130c in the same pattern and extend proximally along the graft 120 and through the fenestrations 170a-d disposed in the proximal portion 124 of the graft 120 (or through connecting members, such as loops of suture or wire, disposed at substantially the same positions on the graft 120 as the fenestrations 170a-d), as described above in connection with the embodiments shown in FIG. 4.

During assembly, as shown in FIG. 5, the proximal ends of the diameter reducing members 160 are held stationary while the distal end of the diameter reducing members 160 are pulled in the distal direction and fixed to the release device 44 in a tightened configuration. As the diameter reducing members 160 are tightened, the diameter reducing members 160 straighten, which causes the diameter reducing connectors 140 attached to each of the respective stents 130 to be drawn circumferentially toward each other. This in turn pulls the bends of the stents 130 to which the diameter reducing connectors 140 are attached toward each other and causes the portion of the graft material disposed between the bends to form gathers 162. Because the bends are drawn toward each other, the stents 130 become partially compressed, which partially reduces the overall diameter of the stent-graft 112 in the intermediate portion 126 of the graft 120. This compression of the stents 130a, 130b, and 130c also draws the bottom portion of the stent-graft 112 in FIG. 5 toward the cannula 106 in the intermediate portion, thereby creating an overall curved configuration along the length of the stent-graft 112. Additionally, when the first and second diameter reducing members 160 are tightened, in the proximal portion 124 of the graft, the portion of the graft disposed between the fenestrations 170a and 170d on both the first and second sides 121, 122 of the graft 120, are drawn upward toward the cannula 106. As the diameter reducing members 160 reach their fully tightened state on both sides of the stent-graft 121, 122, they force the proximal portion 124 of the stent-graft 112 to assume a compressed, reduced diameter configuration having a three lobed shape with three distinct lobes 180a, 180b, and 180c, as shown in FIG. 5a. In the embodiment shown in FIG. 5a, the fenestrations 170a and 170d may be circumferentially clocked away from the tangent line 123 in the clockwise direction by about 120 degrees on the first side 121 of the graft and about 120 degrees in the counterclockwise direction on the second side 122 of the graft. In this configuration, the portion of the graft 120 disposed at the tangent line 123a, and the portions of the graft 120 disposed between the fenestrations 170a and 170d on the first side 121 of FIG. 4, and the portion of the graft 120 disposed between the same fenestrations located on second side 122 of the graft 120 essentially trisect the graft 120 circumferentially into three substantially equal portions. Thus, when the diameter reducing members 160 are tightened and the portions of the graft disposed between the fenestrations 170a and 170d of the first and second sides 121, 122 are drawn toward the cannula 106, the proximal portion 124 forms three lobes having essentially the same size and shape (see FIG. 5a).

Alternatively, as shown in FIG. 5b, in an another embodiment, the fenestrations 170a and 170d may be circumferentially clocked away from the tangent line 123 by an amount that is less than 120 degrees. The distance that the fenestrations 170a and 170d are clocked away from the tangent line 123 on the first side 121 may be the same or different than the distance or degree of clocking on the second side 122. In either case, because the distance(s) of circumferential clocking for the fenestrations 170a and 170d of the first and second sides 121, 122 are less than 120 degrees, the portion of the graft 120 disposed between the fenestrations 170a, 170d of the first and second sides 121, 122 (which is also disposed opposite the cannula 106 and the upper tangent line 123) is larger than the portion of the graft 120 between the fenestrations 170a, d of the first and second sides and the tangent line 123. Accordingly, when the diameter reducing members 160 are tightened, the lobe 180b is larger than the lobes 180a and 180c, as shown in FIG. 5b.

FIG. 6 illustrates the embodiment of FIG. 5 in which the cannula 106 has a curved configuration that is designed to more closely conform to the curvature of a target site in a vessel, such as the aortic arch. As shown in FIG. 6, the stent-graft 112 is still restrained against the cannula 106 along the tangent line 123. However, because the cannula 106 is curved, the overall shape of the stent-graft 112 takes on a curved configuration.

Figure 8:
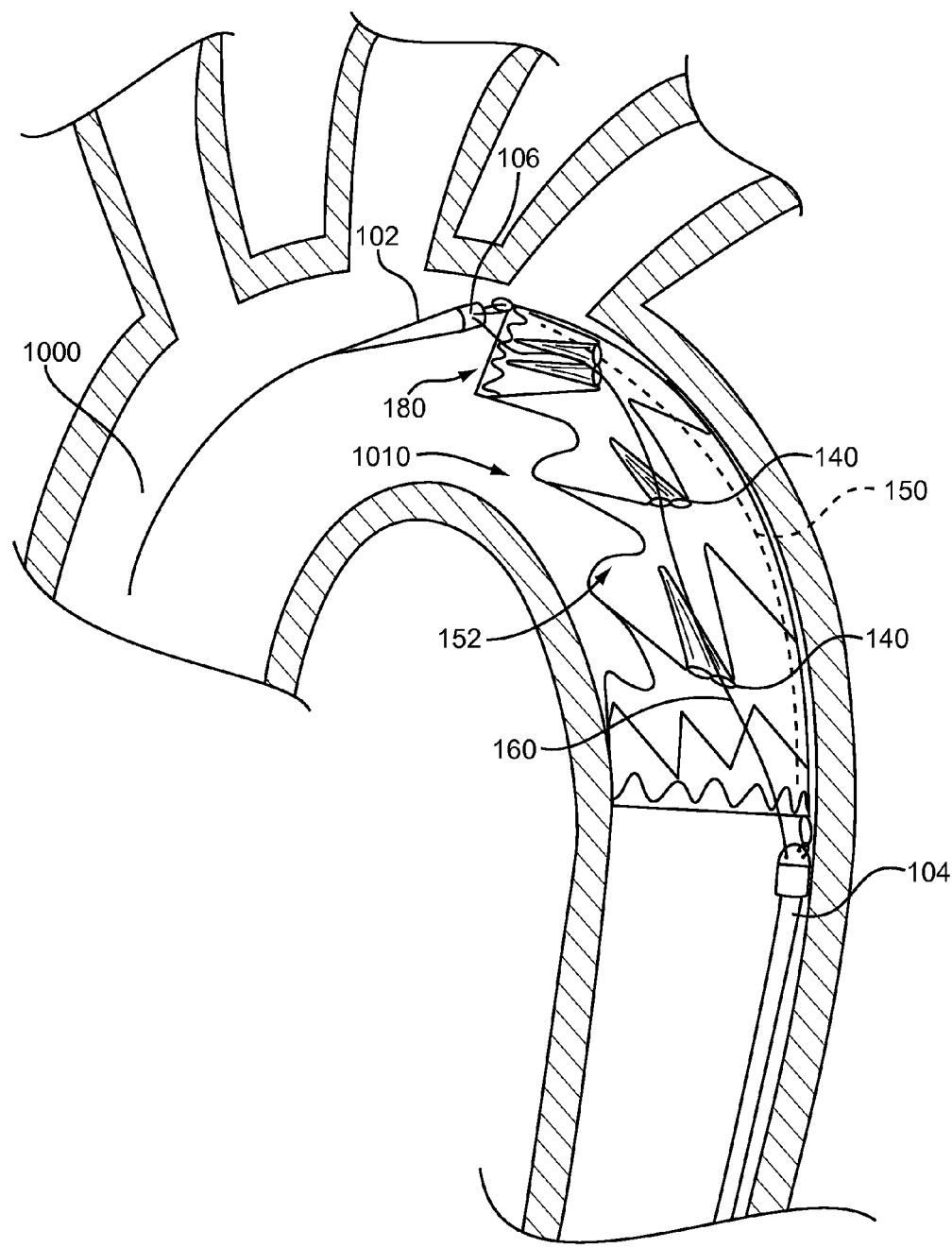
FIG. 8 illustrates the delivery system of FIG. 6 in an initial deployment configuration.
Figure 9:
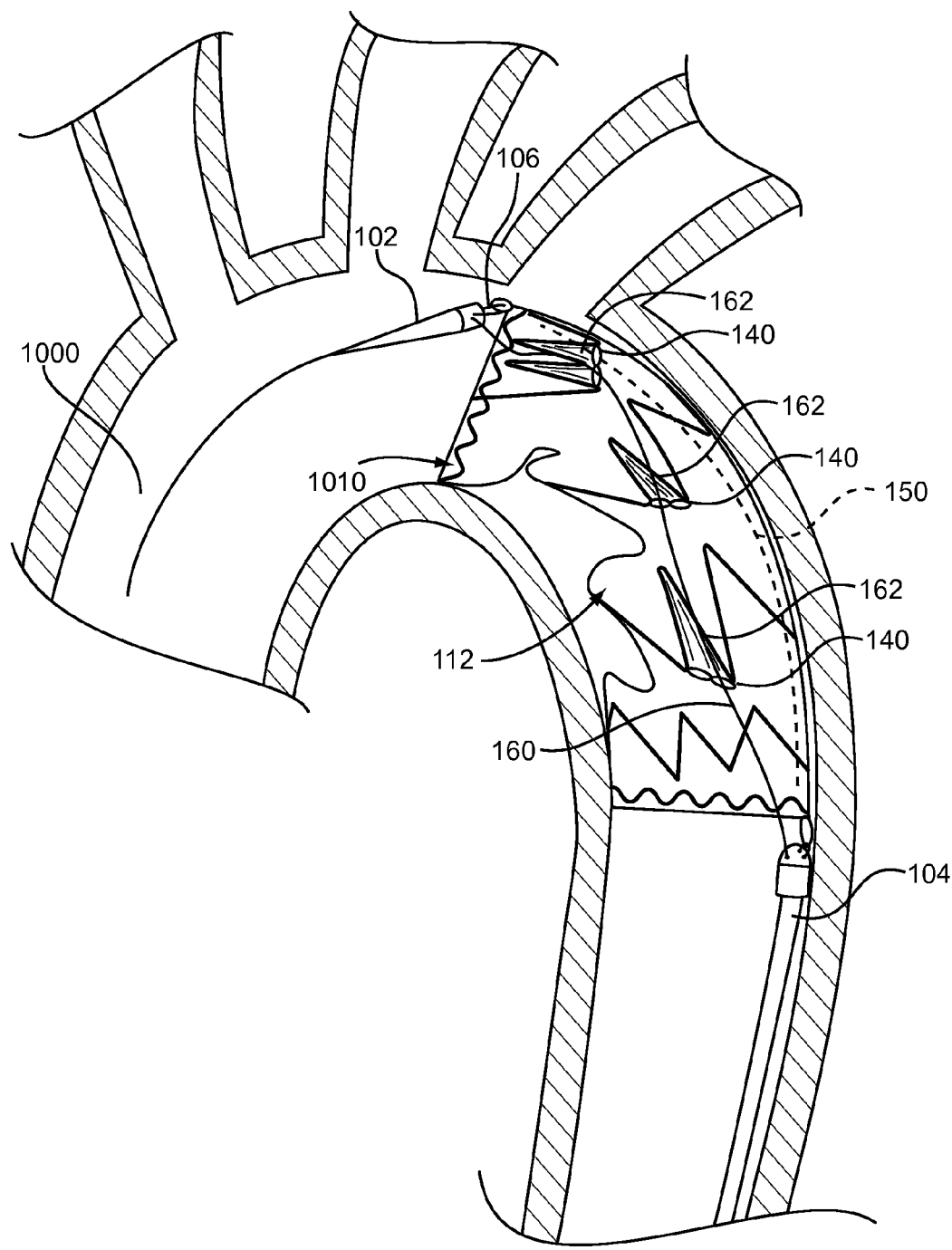
FIG. 9 illustrates the delivery system of FIG. 6 in an intermediate deployment configuration.
Figure 10:
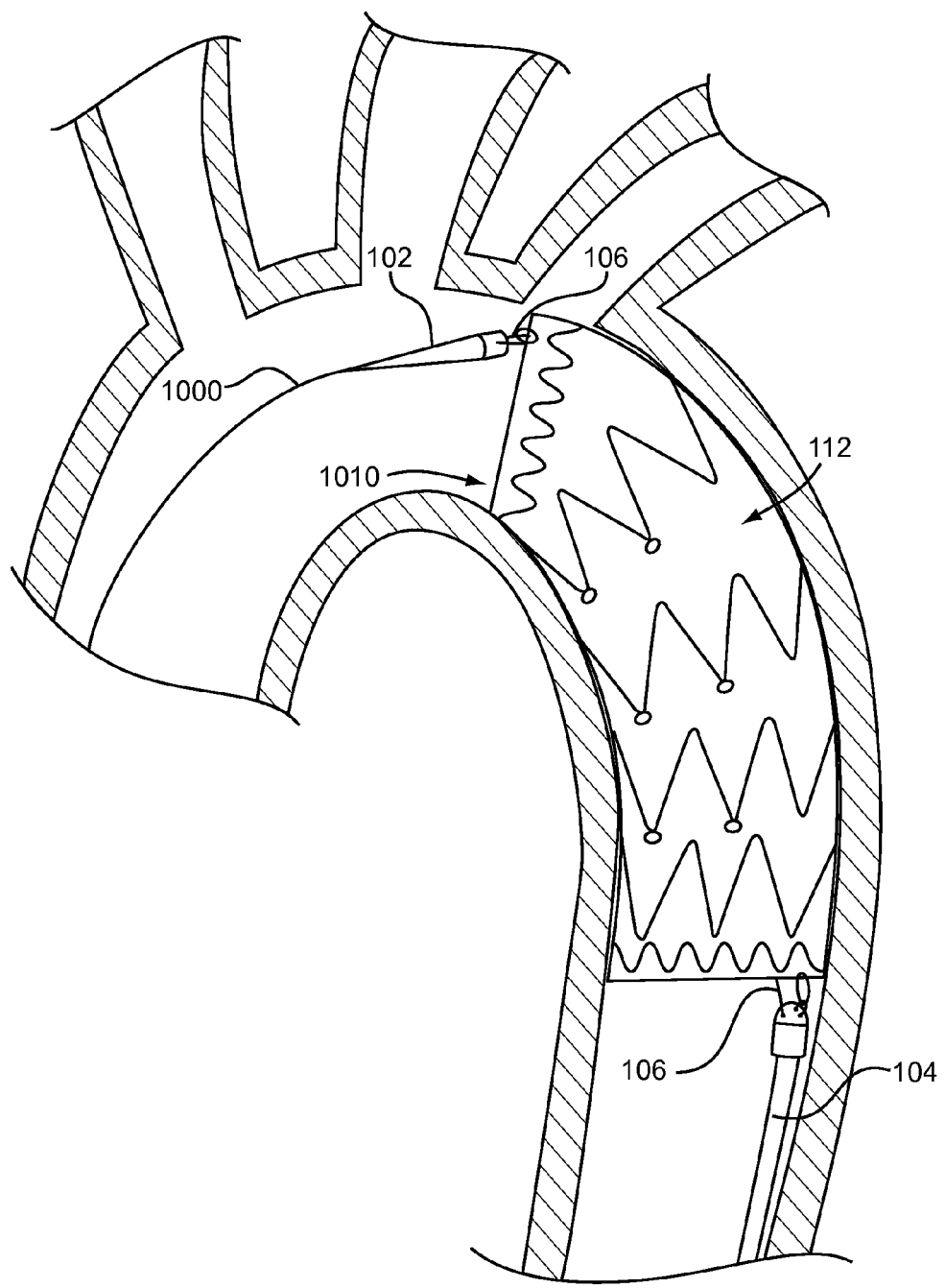
FIG. 10 illustrates the delivery system of FIG. 6 in a fully deployed configuration.

FIGS. 8-10 illustrate a deployment process for the delivery system 100 having a curved cannula 106, as shown in FIG. 7.

Turning to FIG. 8, first, the delivery system 100 is inserted into a patient's vasculature percutaneously and advanced over a guidewire 1000 to the treatment site in the aortic arch or the like using the Seldinger technique, which is well known in the art.

The delivery device 100 may have radiopaque markers disposed on the retention sheath 12 to indicate circumferential orientation of the delivery device 100 and to allow the operator to ensure that the tangent line 123*a*, against which the cannula 106 is restrained, is oriented along the side of the vessel having the greatest radius of curvature. Correspondingly, this also aligns the portions of the stent-graft 112 comprising the reduced diameter connectors 140 and fenestrations 170*a,d* with the side of the vessel having the smallest radius of curvature.

Initially, after the stent-graft 112 has been assembled by tightening the reduced diameter members 160 and the locking member 150, the stent-graft 112 is compressed and restrained in a reduced diameter configuration against the cannula 106 by the retention sheath 12. Once the delivery device 100 is advanced to the treatment site, the sheath 12 is withdrawn and the distal end deployment control mechanism 39 is manipulated to release the distal end of the stent-graft 112. Once released, the distal end of the stent-graft 112 is allowed to expand outward against the vessel wall. When the distal end of the stent-graft 112 is released, blood is still substantially prevented from entering into and passing through the inner lumen of the stent-graft 112, and the majority of the blood flow is directed along the bottom portion of the graft 120 in FIG. 8. This is because the proximal end of the stent-graft 112 is still held in the reduced diameter configuration by the reduced diameter members 160 and the locking member 150. In this way, the proximal end of the stent-graft 112 is not subject to a "wind sock" effect where it is pulled open by the blood flow, which flows in the direction indicated by the arrow 1010, and pushed distally through the vessel and away from its desired placement position.

As shown in FIGS. 8-10, because the cannula 106 is curved and the stent-graft 112 is restrained in a non-coaxial manner against a tangent surface thereof, when the retention sheath 112 is withdrawn the intermediate portion 126 and the proximal portion 124 of the stent-graft 112 remain substantially adjacent or abutting the side of the vessel wall having the greatest radius of curvature. At the same time, the reduced diameter side of the stent-graft 112 is spaced away from the side of the vessel having the smallest radius of curvature. As shown in FIG. 9, once the distal end of the stent-graft 112 has been placed, the diameter reducing members 160 are withdrawn distally in a proximal to distal progression such that the lobes 180 in the proximal portion 124 are released first. Because the top side of the stent-graft 112 in FIG. 8 is already disposed against the portion of the vessel wall having the greatest radius of curvature before the diameter reducing members 160 are withdrawn, the portion of the stent-graft 112 near the tangent line 123*a* is able anchor to the vessel wall along substantially the entire length of the stent-graft 112 while the proximal end of the stent-graft 112 is released. Next, the diameter reducing members are withdrawn from the intermediate portion 126, thereby releasing the stents 130 and the gathers 162, and allowing the remaining portions of the stent-graft 112 to assume their desired expanded, deployed configuration.

In this way, the stent-graft 112 is further able to avoid the pulsatile forces caused by the flow of blood that could push the stent-graft 112 distally away from the desired placement site. Specifically, by ensuring that the top portion of the stent-graft 112 is anchored against the vessel wall before the proximal end is released, the force of the blood flow cannot push the proximal portion distally through the curved vessel and cause the bottom side of the stent-graft 112 to deploy in a position where it does not fully conform to the inner curvature of the vasculature. Thus, a birds beak gap between the stent-graft 112 and the vessel wall is avoided, and the stent-graft 112 is deployed in a configuration that more closely conforms to the curvature of the vessel.

While preferred embodiments have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the features described above are not necessarily the only features of the invention, and it is not necessarily expected that all of the described features will be achieved with every embodiment of the invention.

The invention claimed is:

1. A delivery system comprising:
   a cannula extending from a distal end to a proximal end;
   a stent-graft comprising:
      a tubular graft extending from a proximal end to a distal end, the graft comprising a proximal portion, the graft comprising first and second longitudinally extending sides disposed opposite each other, an intersection of the first and second sides forming a tangent line that extends longitudinally along a length of the graft;
   a locking member extending from the distal end of the cannula, the locking member being movable between a locked position and a released position, wherein, when the locking member is in the locked position, the locking member restrains a surface of the graft against the cannula along the tangent line and a central axis of the cannula is spaced away from a central axis of the graft; and
   a first diameter reducing member, the first diameter reducing member extending from the distal end of the cannula and along a length of the graft, the first diameter reducing member being slidably connected to a first portion of the graft that is disposed closely adjacent to the tangent line in the proximal portion and traversing a lumen of the tubular graft to be slidably connected to a second portion of the graft that is disposed in a position circumferentially spaced away from the tangent line in the proximal portion, the first diameter reducing member having a restrained position and a released position,
   wherein, when the first diameter reducing member is in the restrained position the second portion of the graft is drawn toward the tangent line such that the proximal portion of the stent-graft has a reduced diameter configuration with at least two lobes that extend away from the tangent line and the cannula, and when the first diameter reducing member is in the released position, the second portion is disposed away from the first portion of the graft, the proximal portion of the graft thereby having a substantially tubular configuration.

2. The delivery system of claim 1, further comprising:
   a second diameter reducing member extending from a distal end of the cannula and along a length of the graft, the second diameter reducing member being slidably connected to a third portion of the graft that is disposed closely adjacent to the tangent line in the proximal portion and slidably connected to a fourth portion of the graft that is disposed in a position circumferentially spaced away from the tangent line in the proximal portion, the second diameter reducing member having a restrained position and a released position, wherein, when the first and second diameter reducing members are in the restrained position, the fourth portion of the graft is drawn toward the the tangent line such that the proximal portion of the stent-graft having a reduced diameter configuration with three lobes that extend away from the tangent line and the cannula, and when the first and second diameter reducing members are in the released position, the second portion is disposed away from the first portion of the graft, the proximal portion of the graft thereby having the substantially tubular configuration.

3. The delivery system of claim 1, wherein the proximal portion comprises at least one first side lower fenestration spaced circumferentially away from the tangent line on the first side of the graft, and at least one upper fenestration disposed closely adjacent to the tangent line, wherein the first diameter reducing member extends along the first side of the graft, and wherein the first diameter reducing member extends through the lower fenestration, through the at least one upper fenestration, and to the proximal end of the cannula.

4. The delivery system of claim 3, further comprising:

at least one second side lower fenestration spaced circumferentially away from the tangent line on the second half of the graft; and a second diameter reducing member slidably connected to the distal end of the cannula, the second diameter reducing member extending along the second side of the graft in the proximal portion, through the second side lower fenestration, through the at least one upper fenestration, and to the proximal end of the cannula, the second diameter reducing member being movable between a restrained position and a released position, wherein, when the first and second diameter reducing members are in the restrained position, portions of the graft disposed proximate to the first side lower fenestrations and the second side lower fenestration are drawn toward a portion of the graft disposed proximate to the at least one upper fenestration, the proximal portion of the stent-graft thereby having a reduced diameter configuration with at least three lobes.

5. The delivery system of claim 4, wherein the at least one first side lower fenestration comprises a first and second fenestration and the at least one upper fenestration comprises third and fourth fenestrations, wherein the first diameter reducing member extends: 1) along the graft in the proximal portion, 2) through the first fenestration, 3) through the third fenestration, 4) through the fourth fenestration, 5) through the second fenestration, and 6) to the proximal end of the cannula.

6. The delivery system of claim 5, wherein the at least one second side lower fenestration comprises a fourth and fifth fenestration and the at least one upper fenestration further comprises fifth and sixth fenestrations, wherein the second diameter reducing member extends: 1) along the second side of the graft in the proximal portion, 2) through the fifth fenestration, 3) through the seventh fenestration, 4) through the eighth fenestration, 5) through the sixth fenestration, and 6) to the proximal end of the cannula.

7. The delivery system of claim 6, wherein a portion of the graft disposed between the first and second fenestrations is circumferentially spaced away from the tangent line by about 120 degrees on the first side of the graft, and wherein a portion of the graft disposed between the third and fourth fenestrations is circumferentially spaced away from the tangent line by about 120 degrees on the second side of the graft, and wherein, when the first and second diameter reducing members are in the restrained position, the three lobes are substantially the same size.

8. The delivery system of claim 6, wherein a portion of the graft disposed between the first and second fenestrations is circumferentially spaced away from the tangent line by a first distance on the first side, and wherein a portion of the graft disposed between the fifth and sixth fenestrations is circumferentially spaced away from the tangent line by a second distance on the second side of the graft.

9. The delivery system of claim 8, wherein the first and second distances are the same, the first and second distances being less than ⅓ of the circumference of the graft, whereby, when the first and second diameter reducing members are in the restrained position, the lobe including the portion of the graft disposed opposite the tangent line is larger than the remaining two lobes.

10. The delivery system of claim 1, wherein the stent-graft further comprises:

a support structure attached to the graft, the support structure comprising at least a first stent ring, the first stent ring comprising a plurality of structural members connected by bends in an undulating pattern;

a first diameter reducing connector attached to a first bend of the first stent ring;

a second diameter reducing connector attached to a second bend of the first stent ring; and wherein the first ring is attached to an intermediate portion of the graft, and wherein the first and second bends are disposed on the first side of the graft and spaced circumferentially away from the tangent line.

11. The delivery system of claim 10, wherein, in the intermediate portion, the first diameter reducing member extends from the first diameter reducing connector to the second diameter reducing connector, and wherein, when the first diameter reducing member is in the restrained position, the first bend is drawn circumferentially toward the second bend, thereby forming a first gather in the first side of the graft that decreases a diameter of the stent-graft in the intermediate portion.

12. The delivery system of claim 11, further comprising:

second stent ring attached to the intermediate portion of the graft, the second stent ring comprising a plurality of structural members connected by bends in an undulating pattern;

a third diameter reducing connector attached to a first bend of the second stent ring; and a fourth diameter reducing connector attached to a second bend of the second stent ring, wherein the second ring is attached to the intermediate portion of the graft, and wherein the first and second bends of the second ring are disposed on the first half of the graft and circumferentially spaced away from the tangent line, wherein, in the intermediate portion, the first diameter reducing member further extends from the second diameter reducing connector to the third diameter reducing connector, and from the third diameter reducing connector to the fourth diameter reducing connector, and wherein, when the first diameter reducing member is in the restrained position, the first bend of the second stent ring is drawn circumferentially toward the second bend of the second stent ring, thereby forming a second gather in the graft that further decreases the diameter of the stent-graft in the intermediate portion.

13. The delivery system of claim 12, wherein the first and second bends of the first stent ring and the first and second bends of the second stent ring are circumferentially spaced away from the tangent line between 90 and 120 degrees on the first side of the graft.

14. The delivery system of claim 13, wherein the stent-graft further comprises:
a fifth diameter reducing connector attached to a third bend of the first stent ring;
a sixth diameter reducing connector attached to a fourth bend of the first stent ring;
wherein the third and fourth bends of the first stent ring are disposed on the second half of the graft and circumferentially spaced away from the tangent line.

15. The delivery system of claim 14, wherein, in the intermediate portion, a second diameter reducing member extends from the fifth diameter reducing connector to the sixth diameter reducing connector, and
wherein, when the second diameter reducing member is in the restrained position, the third bend of the first stent ring is drawn circumferentially toward the fourth bend of the first stent ring, thereby forming a third gather in the graft that further decreases the diameter of the stent-graft in the intermediate portion.

16. The delivery system of claim 15, further comprising:
a seventh diameter reducing connector attached to a third bend of the second stent ring; and
an eighth diameter reducing connector attached to a fourth bend of the second stent ring,
wherein the third and fourth bends of the second stent ring are disposed on the second half of the graft and circumferentially spaced away from the tangent line,
wherein, in the intermediate portion, the second diameter reducing member further extends from the sixth diameter reducing connector to the seventh diameter reducing connector, and from the seventh diameter reducing connector to the eighth diameter reducing connector, and
wherein, when the second diameter reducing member is in the restrained position, the third bend of the second stent ring is drawn circumferentially toward the fourth bend of the second stent ring, thereby forming a fourth gather in the graft that further decreases the diameter of the stent-graft in the intermediate portion.

17. The delivery system of claim 14, wherein the third and fourth bends of the first stent ring and the third and fourth bends of the second stent ring are circumferentially spaced away from the tangent line between 90 and 120 degrees on the second side of the graft.

18. A method of repairing a damaged or diseased vessel, the method comprising:
providing a delivery system comprising:
a cannula extending from a distal end to a proximal end;
a tubular graft extending from a proximal end to a distal end, the graft comprising a proximal portion, the graft comprising first and second longitudinally extending sides disposed opposite each other, an intersection of the first and second sides forming a tangent line that extends longitudinally along a length of the graft;
a locking member extending from the distal end of the cannula, the locking member being movable between a locked position, and a released position; and
a diameter reducing member extending from the distal end of the cannula and along a length of the graft, the diameter reducing member being slidably connected to a first portion of the graft that is disposed closely adjacent to the tangent line in the proximal portion and traversing a lumen of the tubular graft to be slidably connected to a second portion of the graft that is disposed in a position circumferentially spaced away from the tangent line in the proximal portion, the diameter reducing member having a restrained position and a released position;
restraining a surface of the graft against the cannula along the tangent line and displacing a central axis of the cannula away from a central axis of the graft by moving the locking member to the locked configuration;
forming a reduced diameter configuration in the proximal portion of the stent-graft having at least two lobes by moving the first diameter reducing member to the restrained position and draw the second portion of the graft toward the tangent line;
advancing the delivery system into a curved lumen; and
moving the diameter reducing member to the released position,
whereby the proximal portion of the stent-graft is released from the reduced diameter configuration and the proximal portion of the stent-graft assumes a substantially tubular configuration.

19. A delivery system for deploying a stent-graft in a curved lumen, the deployment system comprising:
a curved cannula extending in an arced configuration from a distal end to a proximal end;
a stent-graft, the stent-graft comprising:
a tubular graft having a proximal portion and an intermediate portion, the graft comprising first and second longitudinally extending sides disposed opposite each other, an intersection of the first and second sides forming a tangent line that extends longitudinally along a length of the graft,
wherein the proximal portion comprises: 1) first and second fenestrations circumferentially spaced away from the tangent line on the first side of the graft; 2) third and fourth fenestrations circumferentially spaced away from the tangent line on the second side of the graft; and 3) fifth through eighth fenestrations disposed closely adjacent to the tangent line;
a locking member extending from the distal end of the cannula the locking member being movable between a locked position, and a released position, wherein, when the locking member is in the locked position, the locking member restrains a surface of the graft against the cannula along the tangent line, and a central axis of the cannula is spaced away from a central axis of the graft; and
a first diameter reducing member extending from the distal end of the cannula and along the graft, the first diameter reducing member extending in the proximal portion of the graft in order: 1) along the graft in the proximal portion, 2) through the first fenestration, 3) through the fifth fenestration, 4) through the sixth fenestration, 5) through the second fenestration, and 6) to the proximal end of the cannula;
a second diameter reducing member extending from the distal end of the cannula and along the graft, the second diameter reducing member extending in the proximal portion of the graft in order: 1) along the second side of the graft in the proximal portion, 2) through the third fenestration, 3) through the seventh fenestration, 4) through the eighth fenestration, 5) through the fourth fenestration, and 6) to the proximal end of the cannula,
wherein when the first and second diameter reducing members are in a restrained position, a portion of the graft disposed between the first and second fenestrations is drawn toward the tangent line, and a portion of the graft disposed between the third and fourth fenestrations is drawn toward the tangent line, the proximal portion of the stent-graft thereby having a reduced diameter configuration with three lobes.

20. The delivery system of claim 19, further comprising:

a support structure attached to the graft, the support structure comprising at least a first stent ring, the first stent ring comprising a plurality of structural members connected by bends in an undulating pattern;

a first diameter reducing connector attached to a first bend of the first stent ring;

a second diameter reducing connector attached to a second bend of the first stent ring;

a third diameter reducing connector attached to a third bend of the first stent ring;

a fourth diameter reducing connector attached to a fourth bend of the first stent ring, wherein the first stent ring is attached to the intermediate portion of the graft, wherein the first and second bends are disposed on the first side of the graft and circumferentially spaced away from the tangent line, and wherein the third and fourth bends are disposed on the second side of the graft and circumferentially spaced away from the tangent line;

wherein, in the intermediate portion, the first diameter reducing member extends along the second side of the graft to one of the third or fourth diameter reducing connectors and further to one of the first or second diameter reducing connectors, and the second diameter reducing member extends along the first side of the graft from the other of the first or second diameter reducing connectors to the other of the first or second diameter reducing connectors, and wherein, when the first and second diameter reducing members are in the restrained position, the first and second bends are drawn toward the third and fourth bends, thereby forming at least one gather in the graft that decrease the diameter of the stent-graft in the intermediate portion.

21. The delivery system of claim 20, wherein the portion of the graft disposed between the first and second fenestrations is circumferentially spaced away from the tangent line by about 120 degrees on the first side of the graft, and wherein the portion of the graft disposed between the third and fourth fenestrations is circumferentially spaced away from the tangent line by about 120 degrees on the second side of the graft, wherein, when the first and second diameter reducing members in the restrained position, the three lobes are substantially the same size.

* * * * *